(12) United States Patent
Reitan et al.

(10) Patent No.: US 7,517,969 B2
(45) Date of Patent: Apr. 14, 2009

(54) PROCESS FOR ISOLATING NUCLEIC ACID WITH CHAOTROPE AGENTS AND AMMONIUM COMPOUNDS

(75) Inventors: Evy Reitan, Oslo (NO); Arne Deggerdal, Asker (NO); Vidar Skagestad, Haslum (NO)

(73) Assignee: QIAGEN GmbH, Hilden (DE)

( * ) Notice: Subject to any disclaimer, the term of this patent is extended or adjusted under 35 U.S.C. 154(b) by 0 days.

(21) Appl. No.: 10/509,722

(22) PCT Filed: Apr. 2, 2003

(86) PCT No.: PCT/IB03/01202

§ 371 (c)(1),
(2), (4) Date: May 16, 2005

(87) PCT Pub. No.: WO03/084976

PCT Pub. Date: Oct. 16, 2003

(65) Prior Publication Data

US 2005/0214765 A1    Sep. 29, 2005

(30) Foreign Application Priority Data

Apr. 5, 2002    (GB)    ................................ 0207975.4

(51) Int. Cl.
*C07H 21/00* (2006.01)
*C01B 33/12* (2006.01)
*C01B 33/14* (2006.01)

(52) U.S. Cl. ..................... 536/22.1; 536/23.1; 423/335; 423/352

(58) Field of Classification Search ........................ None
See application file for complete search history.

(56) References Cited

U.S. PATENT DOCUMENTS

| | | | |
|---|---|---|---|
| 5,234,809 A | 8/1993 | Boom et al. ................... 435/91 |
| 5,990,302 A * | 11/1999 | Kuroita et al. .............. 536/25.4 |
| 6,027,945 A | 2/2000 | Smith et al. .................. 436/526 |
| 6,090,288 A | 7/2000 | Berglund et al. ............ 210/635 |
| 6,111,096 A * | 8/2000 | Laugharn et al. ............ 204/601 |
| 6,270,970 B1 | 8/2001 | Smith et al. ..................... 435/6 |
| 7,022,835 B1 * | 4/2006 | Rauth et al. ................. 536/25.4 |
| 2002/0106686 A1 * | 8/2002 | McKernan ..................... 435/6 |

FOREIGN PATENT DOCUMENTS

| | | | |
|---|---|---|---|
| EP | 0261955 A2 * | 3/1988 |
| EP | 0 540 170 A1 | 5/1993 |
| EP | 0 969 090 A1 | 1/2000 |
| EP | 1 018 549 A1 | 7/2000 |
| WO | WO 87/06621 | 11/1987 |
| WO | WO9961603 A1 * | 12/1999 |
| WO | WO0119980 A1 * | 3/2001 |
| WO | WO 03/040364 A1 | 5/2003 |

OTHER PUBLICATIONS

Alleman, J. Free Ammonia-Nitrogen Calculator & Information [online], Dec. 24, 1998, [retrieved on Jul. 18, 2007], retrieved from the Internet: <cobweb.ecn.purdue.edu/~piwc/w3-research/free-ammonia/nh3.html>.*
Horne et al (1999) Immobilisation of thiabendazole specific antibodies on an agarose matrix for application in immunoaffinity chromatography. Analyst 124:87-90.*
Dahle C. E. and MacFarlane D. E., "Isolation of RNA from Cells in Culture Using Catrimox-14™ Cationic Surfactant," *BioTechniques*, vol. 15, No. 6, 1993, pp. 1102-1105.
Nguyen, H-K., et al., "Smoothing of the thermal stability of DNA duplexes by using modified nucleosides and chaotropic agents," *Nucleic Acids Research*, vol. 27, No. 6, 1999, pp. 1492-1498.
Prusiner S. B., et al., "Thiocyanate and hydroxyl ions inactivate the scrapie agent," *Proc. Natl. Acad. Sci. USA*, vol. 78, No. 7, Jul. 1981, pp. 4606-4610.
Rudi, Knut, et al., "Quantification of Toxic Cyanobacteria in Water by Use of Competitive PCR Followed by Sequence-Specific Labeling of Oligonucleotide Probes," *Applied and Environmental Microbiology*, 64(7):2639-2643, Jul. 1998.
Rudi, Knut, et al., "Application of Sequence-Specific Labeled 16S rRNA Gene Oligonucleotide Probes for Genetic Profiling of Cyanobacterial Abundance and Diversity by Array Hybridization," *Applied and Environmental Microbiology*, 66(9):4004-4011, Sep. 2000.

* cited by examiner

*Primary Examiner*—Young J Kim
*Assistant Examiner*—Samuel Woolwine
(74) *Attorney, Agent, or Firm*—Seed Intellectual Property Law Group PLLC

(57) ABSTRACT

A process for isolating nucleic acid from a nucleic acid-containing sample, which comprises: (a) providing a chaotrope; (b) providing a nucleic acid binding solid phase capable of binding nucleic acid in the presence of the chaotrope; (c) providing a source of $NH_4^+$ or $NH_3$; (d) contacting the sample with the nucleic acid binding solid phase in the presence of a liquid phase comprising the chaotrope and the $NH_4^+$ or $NH_3$; and (e) optionally separating the solid phase with the nucleic acid bound thereto from the liquid phase.

18 Claims, 1 Drawing Sheet

PROCESS FOR ISOLATING NUCLEIC ACID WITH CHAOTROPE AGENTS AND AMMONIUM COMPOUNDS

FIELD OF THE INVENTION

The present invention relates to a process for isolating nucleic acid from a nucleic acid-containing sample, and to a kit therefor.

BACKGROUND TO THE INVENTION

Procedures involving nucleic acids such as DNA and RNA continue to play a crucial role in biotechnology. Nucleic acid detection and manipulation including hybridisation, amplification, sequencing and other processes generally require nucleic acid to have been isolated from contaminating material. Where a nucleic acid-containing sample is a biological sample, contaminating material may include proteins, carbohydrates, lipids and polyphenols. Accordingly, a variety of approaches have hitherto been used in the isolation of DNA or RNA.

Early methods of isolating nucleic acid involved a series of extractions with organic solvents, involving ethanol precipitation and dialysis of the nucleic acids. These early methods are relatively laborious and time-consuming and may result in low yield. Isopropanol may also be used in the precipitation of the nucleic acid.

U.S. Pat. No. 5,234,809 describes a procedure to isolate DNA from biological samples which uses a chaotropic agent together with a silica based nucleic acid binding solid phase. Guanidine hydrochloride at pH 3 to 5 or guanidine thiocyanate at higher pH, combined with other salts, is used as the chaotropic agent. After binding of the DNA to the solid surface, the solid phase may be washed with the chaotropic agent to remove any biological contamination followed by treatment with 70% ethanol to remove the chaotrope. The DNA is eluted using water.

A variant on this methodology is described in U.S. Pat. No. 6,027,945. Here, a method is described which also uses a silica-based nucleic acid binding solid phase in the presence of a chaotrope to isolate nucleic acid. According to this method, the silica-based solid phase is magnetic, thereby facilitating separation of the solid phase containing the target nucleic acid from the liquid phase containing contaminants upon application of a magnetic field.

WO96/18731 also uses magnetic particles to bind nucleic acid. In this disclosure the magnetic particles are polystyrene-based and polyurethane-coated and a detergent is used instead of a chaotrope.

In spite of the advances made using nucleic acid binding solid phases, the yield of target material can sometimes be undesirably low. The present invention addresses this disadvantage of the prior art.

SUMMARY OF THE INVENTION

Accordingly, in a first aspect, the present invention provides a process for isolating nucleic acid from a nucleic acid-containing sample, which comprises:
(a) providing a chaotrope;
(b) providing a nucleic acid binding solid phase capable of binding nucleic acid in the presence of the chaotrope;
(c) providing a source of $NH_4^+$ or $NH_3$;
(d) contacting the sample with the nucleic acid binding solid phase in the presence of a liquid phase comprising the chaotrope and the $NH_4^+$ or $NH_3$; and
(e) optionally separating the solid phase with the nucleic acid bound thereto from the liquid phase.

In a second aspect, the present invention provides a kit for isolating nucleic acid from a nucleic acid-containing sample, which kit comprises:
(a) a chaotrope;
(b) a nucleic acid binding solid phase capable of binding nucleic acid in the presence of the chaotrope; and
(c) a source of $NH_4^+$ or $NH_3$.

It has surprisingly been found that the presence of $NH_4^+$ or $NH_3$ in the process for isolating nucleic acid gives an increased yield of nucleic acid compared to cases where $NH_4^+$ or $NH_3$ are absent.

Without wishing to be bound by theory, it is thought that the addition of ammonia or ammonium to, say, the chaotropic binding solution, causes the pH to increase by one unit (i.e. from 7.5 to 8.5). However, the resulting increased yield of isolated nucleic acid is not believed to be purely a pH effect. If the pH of the chaotropic solution is increased to 8.5 simply by the addition of alkali, this does not affect the yield of isolated nucleic acid. However, the pH of the solution in the presence of ammonia or ammonium does have an effect on the increased yield of the isolated nucleic acid. Adjusting, say, the chaotropic solution containing ammonia or ammonium back to pH 7.5 with acid does tend to reduce the yield of isolated nucleic acid. Moreover, if the pH exceeds 9.5, the yield of isolated nucleic acid tends to drop. Accordingly, it is preferred that the step of contacting the sample with the nucleic acid binding solid phase in the presence of the $NH_4^+$ or $NH_3$ is conducted at a pH in the range 8.5 to 9.5.

Instead of $NH_4^+$ or $NH_3$, an amine may be used, preferably a primary amine.

The nucleic acid-containing sample typically comprises a biological sample such as a cellular sample. The biological sample may or may not need to be pretreated, depending on its structure. For example, in the case of plant or fungal cells or solid animal tissue, pretreatment would be required as is known in the art. Samples stored in the form of a solid phase such as a paraffin section may also need pretreatment. Samples may be from foodstuffs, environmental samples or clinical samples and may contain prokaryotic or eukaryotic cells or other moieties such as mycoplasmas, protoplasts or viruses. Blood products are an important area for nucleic acid isolation and the present invention is particularly applicable to whole blood and other blood products such as plasma, serum and buffycoat.

The nucleic acid to be isolated may be DNA, RNA or a modified form thereof. Where the nucleic acid is DNA, this may be ds or ss DNA. Where the nucleic acid is RNA, this may be rRNA, mRNA or total RNA.

The chaotrope generally comprises a chaotropic ion provided at a concentration sufficiently high to cause the nucleic acid to lose its secondary structure and, in the case of double-stranded nucleic acids, to melt. Chaotropes are thought to disrupt hydrogen-bonding in water so as to make denatured nucleic acid more stable than its undenatured counterpart. The chaotrope typically comprises a guanidinium salt, urea, or an iodide, chlorate, perchlorate or (iso)thiocyanate. Preferred chaotropes include guanidinium thiocyanate, and guanidinium hydrochloride.

The concentration of chaotrope typically present when contacted with the sample is in the range 2 M to 8 M.

The nucleic acid binding solid phase must be capable of binding nucleic acid in the presence of the chaotrope but is not limited to any specific material. Various materials are now known as nucleic acid binding solid phases and these include silica-based materials such as those described in U.S. Pat. No.

5,234,809, polymeric materials including latex and polystyrene-based materials such as those described in WO96/18731 and other materials such as glasses.

The form of the solid phase includes sheets, sieves, sinters, webs and fibres. Particles are particularly useful as these may be packed in a column or used in suspension and have high binding capacity. Magnetic particles are particularly preferred because of the ease with which they merely separated from an associated liquid phase in a magnetic field. Typical materials for use in magnetic particles include magnetic metal oxides especially the iron oxides. Useful magnetic oxides include iron oxides in which, optionally all or a part of the ferrous iron thereof is substituted with a divalent transition metal such as cadmium, chromium, cobalt, copper, magnesium, manganese, nickel, vanadium and/or zinc. Silica-based magnetic particles useful in the present invention include those described in U.S. Pat. No. 6,027,945 and U.S. Pat. No. 5,945,525.

The source of $NH_4^+$ or $NH_3$ is typically an ammonia solution although other possible sources include those capable of generating ammonia by a chemical reaction or transformation. In order for the $NH_4^+$ or $NH_3$ to be present when the sample is contacted with the nucleic acid binding solid phase, there is no particular limitation on how the $NH_4^+$ or $NH_3$ should be provided. Conveniently, the $NH_4^+$ or $NH_3$ can be provided with the chaotrope, although the technical effect provided by the invention also allows the $NH_4^+$ or $NH_3$ to be provided with the solid phase or even the sample. A potential advantage does arise if the chaotrope and $NH_4^+$ or $NH_3$ are provided together, however. The process according to the invention may further comprise a lysis step comprising subjecting the biological sample to conditions to lyse the sample. This is typically carried out so as to disrupt cells and release their nucleic acid. Lysis conditions conveniently involve the presence of a detergent. It is thought potentially advantageous for the $NH_4^+$ or $NH_3$ to be present during the lysis step as this may have the beneficial effect of increasing yield of nucleic acid during this step. It is also convenient to have the chaotrope present at the same time as this can help the lysis step. Accordingly, where the chaotrope and the $NH_4^+$ or $NH_3$ are provided together as a solution, this solution can be used to treat the biological sample during the lysis step.

The step of separating the solid phase with the nucleic acid bound thereto from the liquid phase is generally required in order to remove contaminants in the liquid phase. Further washing steps may be applied to the solid phase at this point. Any conventional separation step for separating solid phase from liquid phase is applicable, including centrifugation and decanting of the liquid phase from the pelleted solid phase or using a column in which the solid phase is packed and the liquid phase passed through. Where the magnetic solid phase is used, this facilitates separation, which can be carried out in the presence of a magnetic field.

Depending on the form in which the isolated nucleic acid is required, a further elution step can be provided. In some cases it may be satisfactory for the nucleic acid to remain bound to the solid phase. This may be the case if further manipulations of the nucleic acid on a solid phase are required, such as an amplification step. Equally, the nucleic acid may be eluted from the solid phase by applying an elution solution, which may simply be water or a buffer.

BRIEF DESCRIPTION OF THE DRAWINGS

The present invention is now described in more detail, by way of example only, with reference to the following Example and accompanying figure.

DETAILED DESCRIPTION

Example

Figure 1:
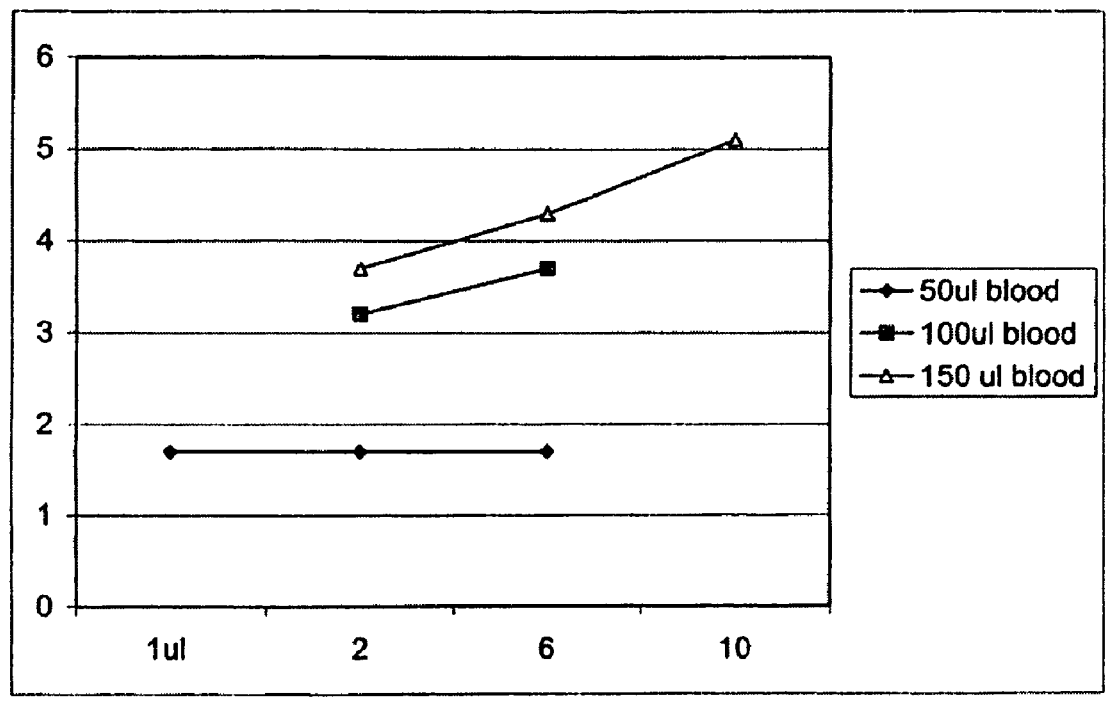
FIG. 1 shows a graph of DNA yield plotted against amount of ammonia in a chaotropic lysis and binding solution.

The magnetic particles. Magnetic Silica particles were obtained in accordance with UK patent application no. 0116359.1 filed on Jul. 4$^{th}$, 2001.

The chaotropic lysis and binding solution. To 130 g Guanidine thiocyanate (Sigma) was added 95 ml 0.1 M TRIS HCl pH 7 (Sigma)+8 ml 0.5 M EDTA (Invitrogen) and 2.5 g tween–20 (Sigma). The solution was heated on a water bath at 30° C. for 1 h. The pH of the solution was 7.5. This solution was used as the reference sample to which no ammonia or ammonium was added. To this solution was added 16 ul 5% $NH_3$ (Merck)/ml chaotropic solution to leave pH at 8.5 as the ammonia or ammonium chaotropic solution described.

The chaotropic wash I solution. To 120 g Guanidine hydrochloride (Sigma) was added water to a total of 160 ml (7.5M)

The ethanol based wash II solution. To 10 ml 4M NaCl (Sigma) was added 100 ul 96% EtOH. To 800 µl of this solution was added 100 ul water.

The DNA binding procedure. 50, 100 and 150 ul of whole blood (WBC 7.7) were added to 720 ul of the chaotropic lysis and binding solution. After 1 min, magnetic silica beads were added (ca 15 mg) and the solution was allowed to incubate for 10 min whereafter the magnetic beads were collected on a magnet. The beads were resuspended in washing solution I and again collected on a magnet. This step was repeated once. The beads were resuspended and washed in washing solution II and collected on a magnet. This step was repeated once. Finally, 100 ul water was added to he beads and they were resuspended at ambient temperature for ca 2 min. The beads were collected on a magnet and the supernatant was transferred to a new tube. The yield of isolated DNA was measured on a Spectrophotometer (Perkin Elmer, Lambda EZ 201).

The results are shown in FIG. 1, in which DNA yield (y-axis) is plotted in arbitrary units against µl of 5% ammonia in the chaotropic lysis and binding solution. The lysis volume is fixed at 760 µl and the solid phase is fixed at 15 mg.

The invention claimed is:

1. A process for isolating nucleic acid from a nucleic acid-containing sample, which comprises:
   (a) providing a chaotrope;
   (b) providing a nucleic acid binding solid phase capable of binding nucleic acid in the presence of the chaotrope;
   (c) providing a source of $NH_4^+$ or $NH_3$;
   (d) contacting the sample with the nucleic acid binding solid phase in the presence of a liquid phase comprising the chaotrope and the $NH_4^+$ or $NH_3$ provide by the source of $NH_4^+$ or $NH_3$, wherein the liquid phase has a pH in the range of 8.5 to 9.5; and
   (e) separating the solid phase with the nucleic acid bound thereto from the liquid phase.

2. The process according to claim 1, which further comprises a step of eluting the nucleic acid from the solid phase.

3. The process according to claim 1, wherein the sample comprises a biological sample.

4. The process according to claim 3, wherein the biological sample comprises a cellular sample.

5. The process according to claim 3, which further comprises a lysis step comprising subjecting the biological sample to conditions to lyse the sample.

6. The process according to claim 5, wherein the source of $NH_4^+$ or $NH_3$ is provided during the lysis step.

7. The process according to claim 1, wherein the nucleic acid to be isolated comprises DNA.

8. The process according to claim 7, wherein the DNA comprises ds DNA.

9. The process according to claim 1, wherein the nucleic acid comprises RNA.

10. The process according to claim 9, wherein the RNA comprises mRNA.

11. The process according to claim 1, wherein the chaotrope comprises a guandinium salt, urea, an iodide, chlorate, perchlorate or (iso)thiocyanate.

12. The process according to claim 1, wherein the nucleic acid binding solid phase comprises a silica-based solid phase.

13. The process according to claim 1, wherein the solid phase is magnetic.

14. The process according to claim 1, wherein the source of $NH_4^+$ or $NH_3$ comprises a solution of ammonia.

15. The process according to claim 1, wherein the source of $NH_4^+$ or $NH_3$ and the chaotrope are provided together as a solution.

16. The process according to claim 7, wherein the DNA comprises ss DNA.

17. The process according to claim 9, wherein the RNA comprises total RNA.

18. The process according to claim 9, wherein the RNA comprises rRNA.

* * * * *